United States Patent [19]

Bara et al.

[11] Patent Number: 5,679,326
[45] Date of Patent: Oct. 21, 1997

[54] DEEP-CLEANSING COMPOSITION CONTAINING PARTICLES OF EXPANDED POLYMER

[75] Inventors: Isabelle Bara, Paris; Myriam Mellul, L'Hay-les-Roses, both of France

[73] Assignee: L'Oreal, Paris, France

[21] Appl. No.: 500,750

[22] Filed: Jul. 11, 1995

[30] Foreign Application Priority Data

Jul. 11, 1994 [FR] France ................... 94 08562

[51] Int. Cl.$^6$ .................................................. A61K 7/02
[52] U.S. Cl. .................... 424/70.1; 424/70.11; 424/63
[58] Field of Search .................... 424/70.1, 70.11, 424/63

[56] References Cited

U.S. PATENT DOCUMENTS 3,645,904  2/1972  Beach ........................................ 252/89
5,510,100  4/1996  Picard ........................................ 424/59

FOREIGN PATENT DOCUMENTS 0502769  9/1992  European Pat. Off. .
0566442  10/1993  European Pat. Off. .
2521003  8/1976  Germany .

*Primary Examiner*—Thurman K. Page
*Assistant Examiner*—D. Faulkner
*Attorney, Agent, or Firm*—Oblon, Spivak, McClelland, Maier & Neustadt, P.C.

[57] ABSTRACT

The invention relates to a deep-cleansing composition including, in a cosmetically and/or dermatologically acceptable medium containing fatty matter, deformable hollow particles which have a particle size of between 80 μm and 300 μm and a density ranging from 15 kg/m$^3$ to 200 kg/m$^3$. These particles are made in particular from an acrylic or styrene-based monomer, acrylonitrile and/or vinylidene chloride.

18 Claims, No Drawings

DEEP-CLEANSING COMPOSITION CONTAINING PARTICLES OF EXPANDED POLYMER

BACKGROUND OF THE INVENTION

1. Field of the Invention:

The invention relates to a deep-cleansing composition usable especially in the cosmetic and/or dermatological fields for massaging, cleaning in depth and/or deep-cleansing the skin of the face, of the neck and/or of the human body. In particular, this composition makes it possible to remove, quite gently, the dead skin cells and impurities from the skin and to unblock the skin pores.

The invention applies to any type of composition and especially to water-in-oil or oil-in-water emulsions, to anhydrous compositions such as pastes or cast products, to lipophilic gels and to lipophilic liquid compositions.

Another subject of the invention is a process for massaging, cleaning and/or deep-cleansing the skin of the body, of the neck and/or of the face.

2. Discussion of the Background:

The purpose of deep-cleansing or exfoliating products, also known by the name of "scrubs", is to make the skin of the face, of the body and/or of the neck softer, and better prepared for the application, particularly of a care product, of make-up or of self-tanning lotion. They are generally in the form of emulsions, as in document CH-678 488. These emulsions contain, as exfoliating particles, polyethylene powder, fine particles of quartz, of vegetable stones or seeds (for example nutshells). These particles generally have mean diameters ranging from 300 µm to 800 µm.

Unfortunately, as a result of the nature (hard, rough) and/or the very size of the exfoliating particles employed, these known exfoliating products generally have the disadvantage of being abrasive, irritating and of being badly tolerated by sensitive skins. Furthermore, these conventional products cause drying out of the skin, especially following an excessive removal of the hydrolipid barrier protecting the epidermis, and this requires, after their application to the skin, the use of a nutrient, protective and/or hydrating cream.

In French Patent Application 93/00990 it has been proposed to produce a deep-cleansing aqueous gel, free from fatty matter and containing microspheres of a copolymer of methyl methacrylate, acrylonitrile and/or vinylidene chloride which have a particle size ranging from 80 µm to 250 µm. As a result of the absence of fatty matter, this gel can, in some cases, draw and even dry out the skin, despite the presence of the microspheres.

There is therefore a continuing need for a composition of the "2 in 1" type requiring no additional treatment of the skin after deep cleansing and not imparting any sticky feel or drying out of the skin.

SUMMARY OF THE INVENTION

The subject of the invention is precisely a deep-cleansing composition comprising a cosmetically and/or dermatologically acceptable medium containing fatty matter, deformable hollow particles which have a particle size ranging from 80 µm to 300 µm and a particle density ranging from 15 kg/m$^3$ to 200 kg/m$^3$.

Despite the small size of the particles, the composition of the invention ensures an efficient deep cleansing and does so without any aggressive action, as a result of their deformability.

DETAILED DESCRIPTION OF THE PREFERRED EMBODIMENTS

"Deformable particles" should be understood to mean flexible and resilient particles which, after crushing, regain their initial shape.

"Fatty matter" should be understood to mean lipophilic compounds such as oils and/or waxy compounds.

These particles advantageously have a particle size ranging from 80 µm to 250 µm and, better, from 120 µm to 250 µm or even from 150 µm to 220 µm.

The particles advantageously have a density ranging from 15 kg/m$^3$ to 200 kg/m$^3$ and, better, ranging from 15 kg/m$^3$ to 150 kg/m$^3$. Surprisingly, the low density of the particles contributes, with their particle size, to the decrease in the greasy feel and to the increase in the softness of the composition of the invention. This characteristic is neither described nor suggested in the state of the art.

According to the invention, it is also possible to produce a virtually anhydrous composition containing less than 10% of water. With this low percentage of water it is quite surprising to obtain no greasy or sticky feel on the skin. Furthermore, the composition of the invention allows the skin to be deep-cleansed while being hydrated, nourished and/or protected.

In addition to these advantages the composition of the invention exhibits a very great softness on application. Furthermore, its appearance is very attractive.

While not wishing to be bound by any particular theory, it is believed that the qualities of the composition of the invention are linked with the deformability of the particles and their low density which, when these spheres are employed in a weight equal to the conventional particles, give products which are much more attractive and efficient.

To obtain this density, particles of expanded polymers or copolymers are advantageously employed, preferably based on vinylidene chloride, acrylonitrile, vinyl chloride, acrylic or styrene-based monomer or based on a mixture of these monomers.

It is possible, for example, to employ a copolymer containing: from 0% to 60% of units derived from vinylidene chloride, from 20% to 90% of units derived from acrylonitrile and from 0% to 50.% of units derived from an acrylic or styrene-based monomer, the sum of the percentages (by weight) being equal to 100. The acrylic monomer is, for example, a methyl or ethyl acrylate or methacrylate. The styrene-based monomer is, for example, α-methylstyrene or styrene. The third monomer is preferably methyl methacrylate. These particles may be in the dry or hydrated state. In particular, the particles may be made of expanded methyl methacrylate/acrylonitrile or methyl methacrylate/acrylonitrile/vinylidene chloride.

In general, the particles usable in the invention may be made of any expanded thermoplastic material which is nontoxic and non-irritating to the skin. They are preferably in the form of microspheres.

The particles of the invention may be obtained, for example, according to the processes of the patents and patent applications EP-56 219, EP-348 372, EP-486 080, EP-320 473, EP-112 807 and U.S. Pat. No. 3,615,972.

The inner cavity of the particles, may contain in principle a gas which may be air, nitrogen or a hydrocarbon such as isobutane or isopentane, carbon dioxide, chlorofluorocarbons or hydrochlorofluorocarbons.

Examples of hollow particles usable in the invention are, in particular, those sold under the trademark EXPANCEL by Nobel Casco, of the DE grade, such as the product 551 DE 80 with a particle size of approximately 80 µm.

From 0.1% to 10% by weight of particles and, better, from 0.3% to 5% and, still better, from 0.3% to 1.5%, relative to the total weight of the composition, is preferably employed in the compositions of the invention. Because of the low density of the particles, a large volume of particles can be incorporated, while retaining a low weight.

Another advantage of the above particles is that they can be employed in a smaller quantity than the particles conventionally employed (2 to 5 wt % in the case of polyethylene powder), as a result of their extremely low density.

Because of this, the products of the invention can be employed daily as soft cleansers or exfoliants or as products for massaging the face and/or the body.

By virtue of the deformable particles and their mechanical action, the composition of the invention gives a massage which is more effective than the particle-free oils or fatty substances generally employed for massage.

The composition of the invention may be a water-in-oil or oil-in-water emulsion, a lipophilic gel, a paste or a cast product which is anhydrous or with a high content of fatty substance. To summarize, the composition of the invention may be in any galenic form containing fatty matter, the latter "fixing" the particles at the surface of the skin and preventing their removal during the massage.

According to the invention the composition may contain from 5% to 99.9% by weight of fatty matter relative to the total weight of the composition and, better, from 10% to 50% by weight even more preferably from 15–30% by weight. The quantity of oil depends, in fact, on the galenic form.

The oils and the waxy compounds usable in the invention as fatty matter may be of mineral, vegetable, synthetic, silicone or fluorine-containing origin. They are those conventionally employed in the cosmetic and/or dermatological field.

By way of examples there may be mentioned: as mineral oil: liquid paraffin or vaseline oil; as vegetable oil: sweet almond, avocado, castor, olive, blackcurrant pip, palm, wheatgerm oil and karite butter; as synthetic oil: caprylic-capric acid triglycerides, octyldodecanol, cetyl alcohol, stearic or stearylic acid and fatty esters such as butyl myristate or isopropyl or octyl palmitate or cetearyl octanoate and isopropyl myristate; as silicone oil: cyclomethicones or polydimethylsiloxanes.

Paraffin wax, jojoba oil and carnauba wax may be mentioned as examples of waxy compounds usable in the invention.

Hydrophilic or lipophilic gelling agents must be employed to obtain a gel. These gelling agents are those conventionally employed in the cosmetic and/or dermatological field.

Examples of gelling agents which may be mentioned are modified clays (bentones) and metal salts of fatty acids (aluminum stearate, ammonium lauryl sulphate, cellulose derivatives, polycarboxyvinyl polymers and fatty alcohols.

In the case of an emulsion, surfactants may be employed for dispersing the fatty matter in water in order to produce oil/water emulsions or vice versa, or for dispersing water in the fatty matter in order to produce water/oil emulsions.

Examples of surfactants which may be employed are fatty acid esters of glycerol or of polyethylene glycol (glyceryl or polyethylene glycol stearate) or of sugar (sorbitan stearate).

The oily compositions of the invention may additionally contain various ingredients conventionally employed in the cosmetic and/or dermatological fields. These ingredients may consist of hydrophilic active substances, lipophilic active substances, perfumes, stabilizers, coloring matter (pigments or dyes), solvents (lower alcohols), clays or else texture agents such as pulverulent agents other than the exfoliating particles. These additional ingredients are employed in the conventional amounts, suitable for the known function.

Examples of hydrophilic active substances which may be mentioned are polyols such as propylene glycol, glycerine and sorbitol. Lipophilic active substances which may be mentioned are the essential oils or oils for removing make-up, such as 2-ethylhexyl palmitate, filters absorbing the ultraviolet and the vitamins.

Another subject of the invention is a process for cleaning and/or deep-cleansing the skin of the body and/or of the face, including the neck, consisting in applying a composition as defined above to the skin, in massaging the skin with this composition to remove dead cells and then rinsing the skin, generally with water, with a view to removing these dead cells and the particles.

Another subject of the invention is the use of the composition defined above for cleaning and/or deep-cleansing the skin of the face, of the neck and/or of the human body.

A further subject of the invention is the use of deformable hollow particles in a cosmetically and/or dermatologically acceptable medium containing fatty matter, for cleaning and/or deep-cleansing the skin of the face, of the neck and/or of the human body, these deformable hollow particles having a particle size of between 80 μm and 300 μm and a density ranging from 15 kg/m$^3$ to 200 kg/m$^3$.

The cleaning of the human body applies equally well to the legs, the arms, the back and the abdomen.

Bearing in mind the non-irritating properties of the composition of the invention, the latter may be employed daily even by people with very dry skin.

Having generally described this invention, a further understanding can be obtained by reference to certain specific examples which are provided herein for purposes of illustration only and are not intended to be limiting unless otherwise specified. The quantities are given in % by weight, based on the total weight of the composition.

EXAMPLE 1

Scrub

Phase A: fatty

| | |
|---|---|
| PEG* 100 and glycerol stearate (surfactant) | 1.2% |
| Polyethylene glycol 20 stearate surfactant) | 1.2% |
| Stearic acid | 0.6% |
| Stearyl alcohol | 0.6% |
| Cetyl alcohol | 0.6% |
| Cetearyl octanoate and isopropyl myristate | 3% |
| Vaseline oil | 15.1% |

*PEG means polyethylene glycol

Phase B: aqueous

| | |
|---|---|
| Glycerol | 3% |
| Stabilizer | 0.5% |
| Distilled water q.s. | 100% |

Phase C:

| | |
|---|---|
| Hollow microspheres of terpolymer** | 2% |

**Particles of expanded acrylonitrile/methyl methacrylate/vinylidene chloride of mean particle size of 210 µm ± 5 µm and with a density of 25 kg/m³ ± 2.

Procedure: Heating phases A and B, separately, 80° C. Emulsification by pouring B into A with energetic stirring with the aid of a turbine at 80° C. Incorporation of phase C in the emulsion with very slow stirring, at 80° C.

A very attractive product is obtained, containing easily visible small spheres, providing a "scrub" effect, very soft to the touch.

EXAMPLE 2

Cleaning Product for the Face

| | | |
|---|---|---|
| Stabilizer | | 0.3% |
| Stearic acid | | 4% |
| Glycerol stearate (surfactant) | | 3% |
| Hollow microspheres of terpolymer* | | 1% |
| Cetyl alcohol | | 4% |
| Ammonium lauryl sulphate (surfactant) | | 5.83% |
| Caprylic-capric acid triglycerides | | 5.5% |
| Propylene glycol (hydrating agent) | | 4.5% |
| Distilled water | q.s. | 100% |

*Particles of expanded acrylonitrile/methyl methacrylate/vinylidene chloride of mean particle size of 185 µm ± 5 and with a density of 44 kg/m³ ± 2.

Procedure: The fatty substances and the surfactants are first all mixed with heating. This fatty phase is then poured into the aqueous phase. The particles are introduced last.

A product of attractive appearance is obtained, for cleaning the face, which is not irritating. The cleaning by virtue of the presence of the terpolymer microspheres is in depth. The treated skin is smooth, soft and well hydrated.

Obviously, numerous modifications and variations of the present invention are possible in light of the above teachings. It is therefore to be understood that within the scope of the appended claims, the invention may be practiced otherwise than as specifically described herein.

This specification is based on French patent application FR 94-08562, filed with the French Patent Office on Jul. 11, 1994, the entire contents of which are hereby incorporated by reference.

What is claimed as new and is desired to be secured by Letters Patent of the United States is:

1. A deep-cleansing oily composition comprising:
   i) a cosmetically and/or dermatologically acceptable medium containing fatty matter; and
   (ii) deformable hollow particles which have a particle size of between 80 µm and 300 µm and a particle density ranging from 15 kg/m³ to 200 kg/m³.

2. The composition of claim 1, wherein said particles have a particle size ranging from 120 µm to 250 µm.

3. The composition of claim 1, wherein said particles are made of an expanded thermoplastic material.

4. The composition of claim 1, wherein said particles are made of a polymer selected from the group consisting of methyl methacrylate, acrylonitrile, vinylidene chloride and copolymers thereof.

5. The composition of claim 1, wherein said particles are made of a copolymer of acrylonitrile, methyl methacrylate and vinylidene chloride.

6. The composition of claim 1, wherein said particles are present in an amount of from 0.3% to 5% based on the total weight of said composition.

7. The composition of claim 1, wherein said fatty matter is present in an amount from 5% to 99.9% based on the total weight of said composition.

8. The composition of claim 1, further comprising at least one adjuvant selected from the group consisting of a gelling agent, a surface-active agent, a hydrophilic active substance, a lipophilic active substance, a perfume, a stabilizer, a solvent, a colorant matter, a wax, a clay, a texture agent and a mixture thereof.

9. The composition of claim 1, wherein said composition is in the form of a water-in-oil or oil-in-water emulsion, of a lipophilic gel, of a paste or of an anhydrous cast product.

10. A method for cleaning and/or deep cleansing the skin of the face, neck and/or human body comprising:
    a) applying a deep-cleansing oily composition to skin;
    b) massaging said skin with said said deep-cleaing oily composition to remove dead cells; and
    c) rinsing said skin,
    wherein said deep-cleaning oily composition comprises:
    i) a cosmetically and/or dermatologically acceptable medium containing fatty matter; and
    ii) deformable hollow particles which have a particle size of between 80 µm and 300 µm and a particle density ranging from 15 kg/m³ to 200 kg/m³.

11. The method of claim 10, wherein said deformable hollow particles have a particle size of between 80 µm and 300 µm and a density ranging from 15 kg/m³ to 200 kg/m³.

12. The method of claim 10, wherein said particles have a particle size ranging from 120 µm to 250 µm.

13. The method of claim 10, wherein said particles are made of an expanded thermoplastic material.

14. The method of claim 10, wherein said particles are made of a polymer selected from the group consisting of methyl methacrylate, vinylidene chloride, acrylonitrile and copolymers thereof.

15. The method of claim 10, wherein said particles are made of a copolymer of vinylidene chloride, acrylonitrile and methyl methacrylate.

16. The method of claim 10, wherein said particles are present in an amount of from 0.3% to 5% by weight based on the total weight of said composition.

17. The method of claim 10, wherein said fatty matter is present in an amount of from 5% to 99.9% by weight based on the total weight of said composition.

18. The method of claim 10, further comprises at least one adjuvant selected from the group consisting of a gelling agent, a surface-active agent, a hydrophilic active substance, a lipophilic active substance, a perfume, a stabilizer, a solvent, a colorant matter, a wax, a clay, a texture agent and a mixture thereof.

* * * * *